(12) United States Patent
Spada et al.

(10) Patent No.: US 11,079,368 B2
(45) Date of Patent: Aug. 3, 2021

(54) OPTICAL-BASED MONITORING AND CHARACTERIZATION OF NATURAL WATER

(71) Applicants: Grace Chang Spada, Santa Barbara, CA (US); Craig A. Jones, Santa Cruz, CA (US); Todd Martin, Salt Lake City, UT (US)

(72) Inventors: Grace Chang Spada, Santa Barbara, CA (US); Craig A. Jones, Santa Cruz, CA (US); Todd Martin, Salt Lake City, UT (US)

(73) Assignee: Integral Consulting Inc., Seattle, WA (US)

( * ) Notice: Subject to any disclaimer, the term of this patent is extended or adjusted under 35 U.S.C. 154(b) by 533 days.

(21) Appl. No.: 15/633,656

(22) Filed: Jun. 26, 2017

(65) Prior Publication Data
US 2018/0038840 A1 Feb. 8, 2018

Related U.S. Application Data (60) Provisional application No. 62/354,641, filed on Jun. 24, 2016.

(51) Int. Cl.
| | | |
|---|---|---|
| *G01N 33/18* | (2006.01) | |
| *G16C 10/00* | (2019.01) | |
| *G16C 20/30* | (2019.01) | |

(52) U.S. Cl.
CPC .............. *G01N 33/18* (2013.01); *G16C 10/00* (2019.02); *G16C 20/30* (2019.02)

(58) Field of Classification Search
CPC .......... G01N 33/18; G16C 10/00; G16C 20/30
See application file for complete search history.

(56) References Cited

U.S. PATENT DOCUMENTS

| | | | | | |
|---|---|---|---|---|---|
| 5,116,759 | A | * | 5/1992 | Klainer ................ | G01N 21/253 385/12 |
| 5,545,517 | A | * | 8/1996 | Thompson ............. | C12Q 1/527 356/301 |

(Continued)

OTHER PUBLICATIONS

Wagner et al, Guidelines and Standard Procedures for Continuous Water-Quality Monitors: Station Operation, Record Computation, and Data Reporting, U.S. Geological Survey, Enterprise Publishing Network, cover-cover (Year: 2006).*

(Continued)

*Primary Examiner* — Lisa E Peters
(74) *Attorney, Agent, or Firm* — Soquel Group Inc.

(57) ABSTRACT

The invention is directed towards a method and system for optically-based monitoring of chemicals of potential concern (COPCs), including mercury (Hg), methyl mercury (MeHg), and polychlorinated biphenyls (PCBs). It employs a multi-parameter statistical analysis model, such as partial least square regression (PLS regression), to identify combinations of predictors (e.g., optical, water quality, and physical properties) that have large covariance with the response values. The predictive model is validated against analytic samples from laboratories. The steps in the method are repeated until predictors, or parameters are selected that avoid over-fitting and which yield physically-based results.

16 Claims, 3 Drawing Sheets

(56) References Cited

U.S. PATENT DOCUMENTS

| | | | | |
|---|---|---|---|---|
| 2005/0118704 A1* | 6/2005 | Malobabic | ............... | G01N 1/14 |
| | | | | 435/287.1 |
| 2005/0151965 A1* | 7/2005 | Bissett, III | ................ | G01J 3/28 |
| | | | | 356/328 |
| 2007/0233397 A1* | 10/2007 | Kim | ..................... | G01N 33/188 |
| | | | | 702/19 |
| 2015/0323514 A1* | 11/2015 | Chen | ...................... | G01N 33/18 |
| | | | | 702/25 |
| 2016/0054281 A1* | 2/2016 | Smeeton | ............. | G01N 21/532 |
| | | | | 250/373 |

OTHER PUBLICATIONS

EMM68 Buoy, Specification Sheet, 2013, Xylem, Inc, YSI Systems (Year: 2013).*

Y. Khan and C. S. See, "Predicting and analyzing water quality using Machine Learning: A comprehensive model," 2016 IEEE Long Island Systems, Applications and Technology Conference (LISAT), Farmingdale, NY, 2016, pp. 1-6, doi: 10.1109/LISAT.2016.7494106. (Year: 2016).*

Mohamad Javad Alizadeh, Mohamad Reza Kavianpour, Malihe Danesh, Jason Adolf, Shahabbodin Shamshirband & Kwok-Wing, Effect of river flow on the quality of estuarine and coastal waters using machine learning models, Engineering Applications of Computational Fluid Mechanics, 12:1, 810-823, DOI: 10.1080 (Year: 2018).*

Guidelines for Drinking-water Quality, Third Edition, World Health Organization, Geneva 2008 (Year: 2008).*

* cited by examiner

OPTICAL-BASED MONITORING AND CHARACTERIZATION OF NATURAL WATER

CROSS-REFERENCE TO RELATED APPLICATIONS

This application claims the benefit of U.S. Provisional Application No. 62/354,641, filed Jun. 24, 2016.

BACKGROUND

The processes controlling chemical concentration variability in natural water bodies often occur on disparate temporal and spatial scales, leading to ambiguity in conventional surface water data sets.

Optically-based monitoring provides continuous, high temporal resolution data and importantly, comprehensive characterization of surface water processes to enable interpretation of chemical concentration variability in the context of physical processes.

Optically-based water quality monitoring research, development, and operational studies have shown that optical properties are effective for, e.g., characterizing particle composition in natural waters. Due to the hydrophobic nature of chemicals of potential concern (COPCs) such as mercury (Hg), methyl mercury (MeHg), and polychlorinated biphenyls (PCBs) and their tendency to associate strongly with organic particles that have unique and identifiable optical signatures, optical measurements thus provide a potential means to quantify the concentration of COPCs. Bergamaschi et al. successfully developed and validated models for the derivation of Hg and MeHg concentration from optical properties for several different tidal estuaries as reported in (Bergamaschi et al. 2011, Methyl mercury dynamics in a tidal wetland quantified using in situ optical measurements. Limnol. Oceanogr. 56:1355-1371). Previous studies have not quantified concentrations of PCBs using in situ optical properties.

A pilot study was conducted for the Berry's Creek Study Area (BCSA) in October 2013 by the inventors to determine the feasibility of predicting organic matter (OM) and COPC concentrations in surface water, specifically Hg, MeHg, and PCBs, from near-continuous measurements of optical properties. The pilot study is described in a report by the Berry's Creek Study Area Cooperating PRP Group, 2017, Berry's Creek Study Area Remedial Investigation Report, currently in review by the U.S. Environmental Protection Agency, New York N.Y. The study followed and built upon methods described by Bergamaschi. The pilot study was highly successful and demonstrated an order of magnitude increase in the number of data points obtainable, continuous in situ assessment of OM and COPC variability, and reliable observations of surface water OM and COPC concentration variability in relation to physical and biogeochemical processes. Therefore, additional optically-based monitoring studies were proposed to the United States Environmental Protection Agency (USEPA), accepted, and conducted in July 2014 and August through October 2015 over several spring-neap tidal cycles to evaluate the sources and variability of COPCs in the surface water of the BCSA. These optically-based monitoring studies were motivated by a need for a better understanding of COPC concentrations in surface water and sources to water column-based exposure pathway, primarily to pelagic fish. The specific objectives of the current study were to: (1) gain an understanding of OM and COPC concentration dynamics in the water column in the BCSA and (2) characterize COPC mobility in the BCSA water column.

The current invention is based, in part, on the methods developed and tested during this study. Based on the findings of the study, it was concluded that an optically-based chemical regression model can provide reliable predictions of surface water COPC and OM concentrations at levels of accuracy and precision comparable to traditional surface water measurements. Further, an optically-based method provides continuous OM and COPC concentration data at high temporal resolution for evaluation relative to physical and biogeochemical parameters, enabling the exploration of COPC source(s) and dynamics.

Thus, it is with respect to these considerations and others that the present invention has been made.

SUMMARY OF THE DESCRIPTION

Various embodiments are directed towards a method and system for optically-based monitoring of chemicals of potential concern (COPCs), including inter alia mercury (Hg), methyl mercury (MeHg), and polychlorinated biphenyls (PCBs).

In certain embodiments, an optically-based chemical monitoring approach employs a multi-parameter statistical analysis technique such as partial least square regression (PLS regression), that combines multiple linear regression and principal component analysis (PCA), where PLS regression finds a combination of predictors that best fit a response and PCA finds combinations of predictors with large variance. Therefore, the multi-parameter statistical regression analysis identifies combinations of predictors (e.g., optical, water quality, and physical properties) that have large covariance with the response values (e.g., COPC and OM data). It combines information about the variances of both the predictors and the observations while also considering the correlations among them. It therefore provides a model with reliable predictive power.

Although multi-parameter statistical regressions are widely used in fields such as chemometrics, innovations include the application to integrated high resolution field measurements of physical, optical, and biogeochemical predictor variables with judiciously sampled discrete, laboratory-based chemical data.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description of the Preferred Embodiment, which is to be read in association with the accompanying drawings, wherein.

DETAILED DESCRIPTION

The invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the invention may be embodied as methods, processes, systems, business methods or devices. Accordingly, the present invention may take the form of an entirely hardware embodiment, an entirely software embodiment or an embodiment combining software and hardware aspects. The following detailed description is, therefore, not to be taken in a limiting sense.

As used herein the following terms have the meanings given below:

Chemicals Of Potential Concern (COPCs)—refers to a chemical that is potentially site related and of sufficient quality to quantify risk. Different jurisdictions define COPCs differently but at a minimum, as used herein, COPCs include mercury (Hg), methyl mercury (MeHg), and polychlorinated biphenyls (PCBs).

The subject invention operates in a variety of water environments, including but not limited to: oceans and seas, ports and harbors, deltas, estuaries, rivers, lakes, and including man-made structures such as storm drains, outfalls, channels, and basins.

The subject invention operates across a complete range of natural and anthropogenic physio-biogeochemical conditions including, for example: upwelling, eddy circulation, phytoplankton blooms, storms, tidal conditions (including inter alia ebb, flood, high slack tide, low slack tide, neap tide), dredging, etc.

The subject invention operates in water with varying depths and levels of clarity and salinity.

Generalized Operation

The operation of certain aspects of the invention is described below with respect to FIGS. 1-2.

Figure 1:
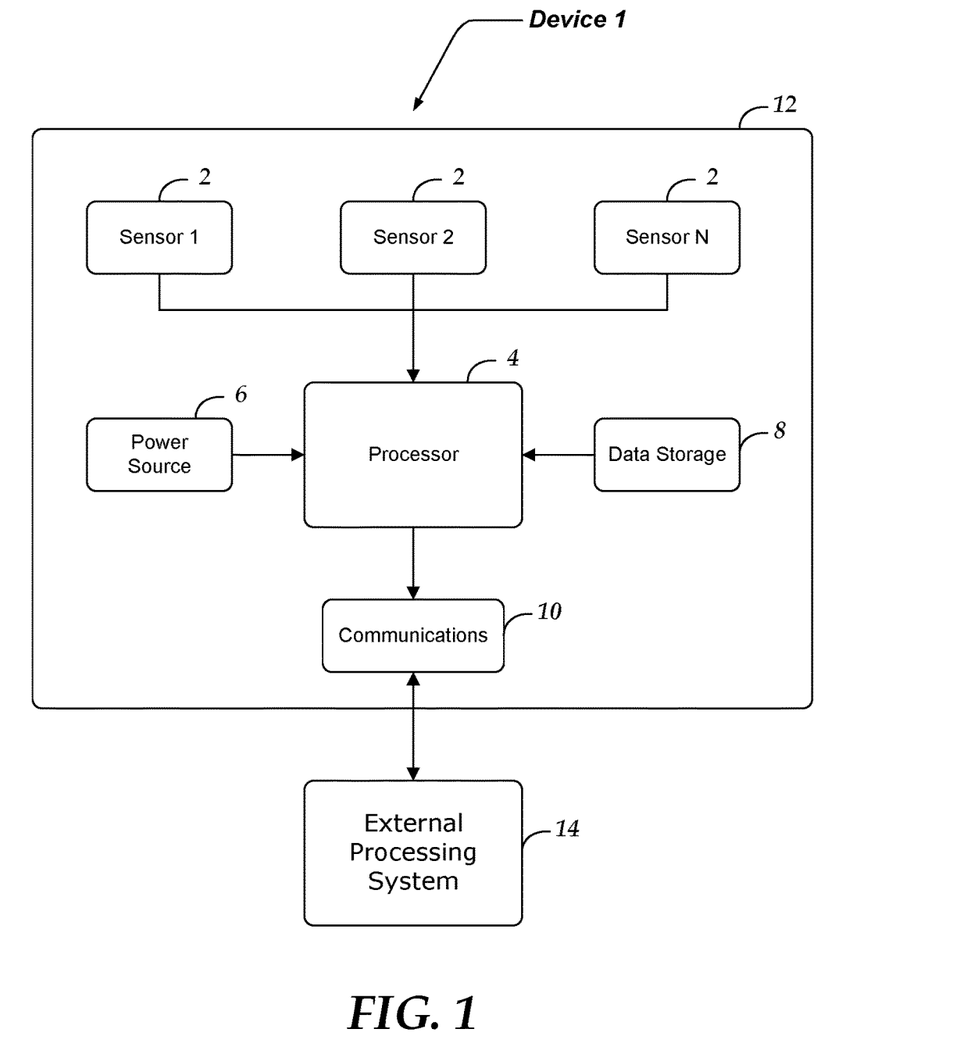
FIG. 1 is a block diagram of an embodiment of an optical-based device for monitoring and characterizing natural waters.

FIG. 1 is a block diagram of an embodiment of an optically-based device 1 for monitoring and characterizing natural waters, referred to herein as characterizing device 1 or simply device 1. Device 1 is intended to be submerged or sampled in-line in a natural or anthropogenic water environment such as an estuary or storm drain for periods of time. It may communicate sensor data in real-time via cellular, radio frequency (RF), or satellite technology and/or upon being retrieved, it may communicate with one or more external devices to provide sensor data and/or to report results.

Device 1 includes one or more environmental monitoring sensors 2 (e.g., physical, optical, acoustical, water quality, etc.) that measure aspects of natural water and/or surrounding environment, and generate a data stream to a processor 4. Processor 4 receives a stream of sensor data from sensors 2 and stores the sensor data in a data storage 8. In certain embodiments, processor 4 is a commercial microprocessor. Alternatively, processor 4 may be implemented using a custom microcontroller, or by a plurality of processors that operate cooperatively. Processor 4 and data storage 8 may be internal (part of sensors 2) or external devices.

Device 1 supports three general classes of embodiments: on-board processing, off-board processing, and partial processing. In on-board processing embodiments, processor 4 performs all or part of the processing on sensor data from sensors 2 that results in a characterization of the water in which device 1 is sampling. In off-board processing embodiments, the processing is deferred in which case data stored in data storage 8 is provided via a communications link 10 to an external processing system 14 for processing. In partial processing embodiments, part of the processing performed on-board by processor 4, then intermediate results are communicated to external processing system 14 which performs the remainder of the processing steps. Further, there are real-time and off-line embodiments where a real-time mode performs some or all of the processing on-board, i.e. sensor data is processed in real-time by device 1 and results or partial results are sent to an external processing system 14 for display, reporting, storage and in some cases additional processing.

Processor 4 receives power from a power source 6, which may be an internal or external commercial DC battery. In certain embodiments, power source 6 may be a combination of power sources including, for example, a battery, an externally mounted solar cell, wind turbine, or wave power generation unit.

A data storage 8 subsystem is also connected to processor 4 enabling processor 4 to store sensor data for later retrieval. In off-board or partial processing embodiments, data storage 8 also stores intermediate or complete results. Data storage 8 also provides nonvolatile memory storage for data and program code. Such storage may be in the form of inter alia random access memory (RAM), read only memory (ROM), flash memory, or disk storage.

Processor 4 interfaces with external devices via a communications 10 subsystem. In one embodiment communications 10 provides a physical connection, for example a cable that connects to a USB or serial interface. In other embodiments, near field communication such as BLUETOOTH are used; in still other embodiments, communication subsystem 10 may communicate remotely to a device on land or on a ship using any of a variety of communications techniques such as cellular, RF, or satellite communications. One example of a satellite communication system that may be used for this purpose is the IRIDIUM satellite network that covers the Earth operated by Iridium Communications Inc. of McLean, Va. This may be a communications line or a wireless link. Alternatively, in certain embodiments device 1 may interface with external devices through a removable data storage, such as a USB drive. In such embodiments, data storage 8 may act as a communications subsystem 10 in addition to storing data.

A housing 12 provides a waterproof enclosure(s) that houses items elements 2-10. Housing 12 can enclose all elements 2-10 or elements 2-10 individually. Housing 12 is typically fabricated from stainless steel, acetal homopolymer, plastic or another water resistant, non-corrosive material. All components of device 1 are securely mounted within the pressure-tested housing. Housing 12 may also include attachment means that enable device 1 to be moored in a natural water environment.

A variety of alternative hardware configurations are possible without departing from the spirit and scope of the subject invention. While it is expected that a minimum hardware configuration will include sensors, power source(s), processor(s), data storage and a communications subsystem(s), some of these components can be omitted in certain other embodiments. For example, data storage may be omitted if sensor data and processed results are transmitted wirelessly in real time. Further communications may be omitted in configurations where data storage is removed, e.g. the case of a USB drive, from device 1 when it is retrieved.

Sensors

A variety of environmental sensors 2 may be used with the subject invention. Each sensor generates one or more series of values, where each series, or parameter, represents a particular physio-biogeochemical characteristic of a water column and/or surrounding environment being monitored, e.g. temperature, absorption, reflectance and backscattering. It is not uncommon for sensors 2 to generate twenty or more parameters, i.e. distinct data streams, e.g., pressure, salinity, current velocity, wave height, water clarity, fluorescence, etc. The following instruments are examples of those that may operate with the subject invention:

Absorption-attenuation meter (a-c meter) for spectral absorption of multiple wavelengths in the visible spectrum (400-730 nm). One such device is provided by Sea-Bird Scientific (formerly WET LABS, INC.) of Philomath, Oreg. Typically, the a-c meter is a flow-through optical sensor. Its absorption intake tube may be outfitted with a filter for direct measurements of dissolved spectral absorption. Copper tubing and copper mesh on the a-c meter intakes may be utilized for biofouling mitigation.

Fluorometers for colored dissolved organic matter (CDOM), chlorophyll-a (Chl-a), or other pigment (phycoerythrin) or chemical concentration. One such device is provided as part of its ECO SENSOR product line by Sea-Bird Scientific.

Scatter or backscatter sensor for backscattering coefficient ($b_b$). One such device is provided as part of its ECO SENSOR product line by Sea-Bird Scientific.

Water quality sonde with probes for conductivity, temperature, depth, turbidity, dissolved oxygen, and pH. One such device is provided by YSI (Yellow Springs, Ohio). Water quality sonde probes may also include those for fluorescence of CDOM and phytoplankton pigments.

Other sensors that may be employed include conductivity sensor, temperature sensor, depth sensor, spectrometer, spectrophotometer, current meter, and nutrient sensor.

Sea-bird Scientific ECO sensors and the YSI turbidity probe are flat-faced optical sensors may be equipped with copper anti-biofouling shutters or bio-wipers for long-term deployments.

In certain embodiments, all measurement windows or intake tubes of all aquatic sensors are located at equal distances above the sediment bed or below the surface of the water. The placement of sensors is determined based on system processes and feasibility of deployment.

Figure 2:
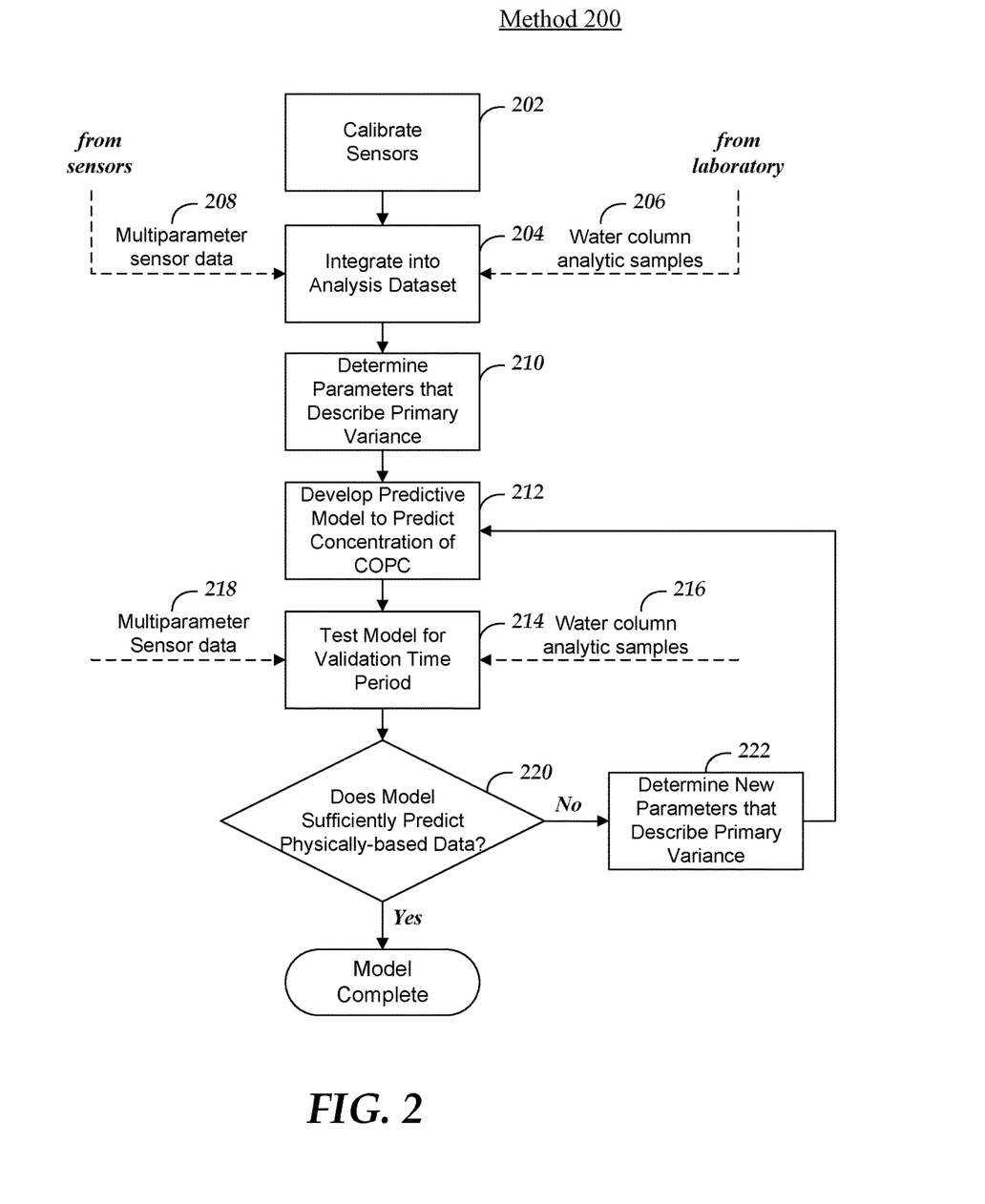
FIG. 2 illustrates one embodiment of a flow diagram for the processing of sensor data by an optically-based device.

FIG. 2 illustrates one embodiment of a flow diagram for a method 200 for monitoring and characterizing natural waters. Generally, method 200, also referred to as the multi-parameter regression method, can be used to characterize a wide variety of surface water and chemicals, including inter alia: dHg, dMeHg, tHg, tMeHg, pHg, pMeHg, and tPCBs (where d and t specify dissolved and total, or unfiltered); and concentrations of total suspended solids, dissolved organic carbon, and particulate organic or inorganic carbon. Modeled particulate components of Hg and MeHg may be determined by both the method 200 and by difference (i.e., modeled unfiltered minus modeled filtered) for validation purposes.

Method 200 is used to characterize the concentrations of a chemical, e.g. a COPC, in a single location in natural water for a period of time, referred to as a calibration time period, based on multi-parameter sensor data 208 from sensors 2. A concentration may be measured in milligrams per liter, for example. Method 200 processing steps may be performed entirely by device 1 or partially by device 1 and partially by one or more external processing systems such as external processing system 14. Generally, each step of method 200 may be performed flexibly by various processing systems without departing from the scope and spirit of the subject invention.

At step 202 sensors 2 are calibrated, typically following protocols that are provided by the manufacturer, or by the scientific community. For example, the ac-s may be calibrated to a purified water standard such as Nanopure water such that the output of the ac-s is the total absorption coefficient minus that of pure water. CDOM and Chl-a concentration from ECO-fluorometer measurements may be factory calibrated or field-calibrated. All ECO sensors may be corrected to dark count calibrations conducted prior to deployment. The YSIs may be calibrated to National Institute of Standards and Technology (NIST) standards. Calibration procedures include resetting each water quality parameter against NIST standard calibration solution. Current meter calibrations may involve internal compass calibration, verification of the functionality of the electronic circuitry and memory, battery tests, and beam continuity checks.

At step 204 two data sets, each representing measurements of a water column to be analyzed for a period of time, are received and are integrated into an analysis dataset. A first data set includes analytic or discrete water column samples 206, also referred to as analytic data, which are provided by a laboratory. In other words, samples of the water column are sent to a laboratory for analysis. The resulting lab report indicates the concentrations of specified chemicals, solids, and/or dissolved material in the water column. A second data set, referred to as multi-parameter sensor data 208 is received, or derived, from the various sensors 2. Sensor data 208 is high resolution, time series, data, from sensors 2 but does not provide the COPC concentration data in a time series format. Thus, as part of an initial calibration both water samples tested by a laboratory and water samples from a variety of sensors are received. Any analytical sample field duplicates may be averaged to obtain a coherent single analysis dataset.

At step 210 a set of parameters are determined that are intended to describe the primary variance of a particular COPC concentration in the water column. Using statistical methods, at this step, the parameters that describe the main variability of COPC over time are determined and selected. The goal is to create a model that explains the concentration of a COPC in the water column, as indicated by the analytic samples, which uses the most important parameters derived from sensor data. For example, if reflectance is determined to have significant influence over the COPC being monitored then it will be determined or selected at this step; on the other hand, temperature may be determined to have little influence over the concentration level of the COPC and will thus not be selected at this step. As will be discussed hereinbelow this set of parameters will be refined if the model fails to sufficiently predict COPC concentrations. The choice of these predictors is based on (1) previous experience, (2) linear regression analysis between environmental variables with analytical data, and (3) prior assessments of optical responses to particulates and dissolved material in field studies.

At step 212, a multi-parameter statistical regression model is developed to model and predict COPC concentrations in a water column. While other statistical method may be used, method 200 has been tested and has shown to be operable when using a multi-parameter statistical algorithm. The predictor data sets for the model may be constructed by matching environmental data to the nearest times of analytical sample collection (i.e. to the response variable time stamps). When using this statistical model, it is important to choose the number of components in the regressions for each of the response variables such that the maximum percent variance in responses is explained without over-constraining, or over-fitting, the model. In other words, the model is optimized to maximize the variance explained while reducing residuals or error. Model over-constraint occurs when the regression simply matches modeled versus measured variables, resulting in predictions that do not consider natural physio-biogeochemical processes. Optical-based chemical model over-constraint causes unreasonable values in predicted COPCs, such as derived concentrations that are less than zero. Component optimization may be performed by systematically increasing the number of components, and subsequently the percent variance, until the variability in the predicted data series becomes stable but before model over-constraint occurs. For example, for determination of dHg, the model may be run first for one component, then for two, then three, etc. until the general time series pattern is consistent (or stable) as a function of the number of components and before strong negativity occurs. An optically-based multi-parameter regression model may be used with the same number of components as parameters or predictors in order to investigate the ranges of variance explained in responses as a function of the total number of components, which is essentially the results of a principal component analysis.

It may be appreciated by one skilled in the art that the step of determining a subset of parameters in order to avoid over-constraining, or over-fitting, the model is novel and innovative in the context of creating a predictive model that potentially has a large number of parameters. While the multi-parameter statistical model is known in the art, it is not sufficient in itself to be used as a predictive model for an application such as that described herein.

Figure 3:
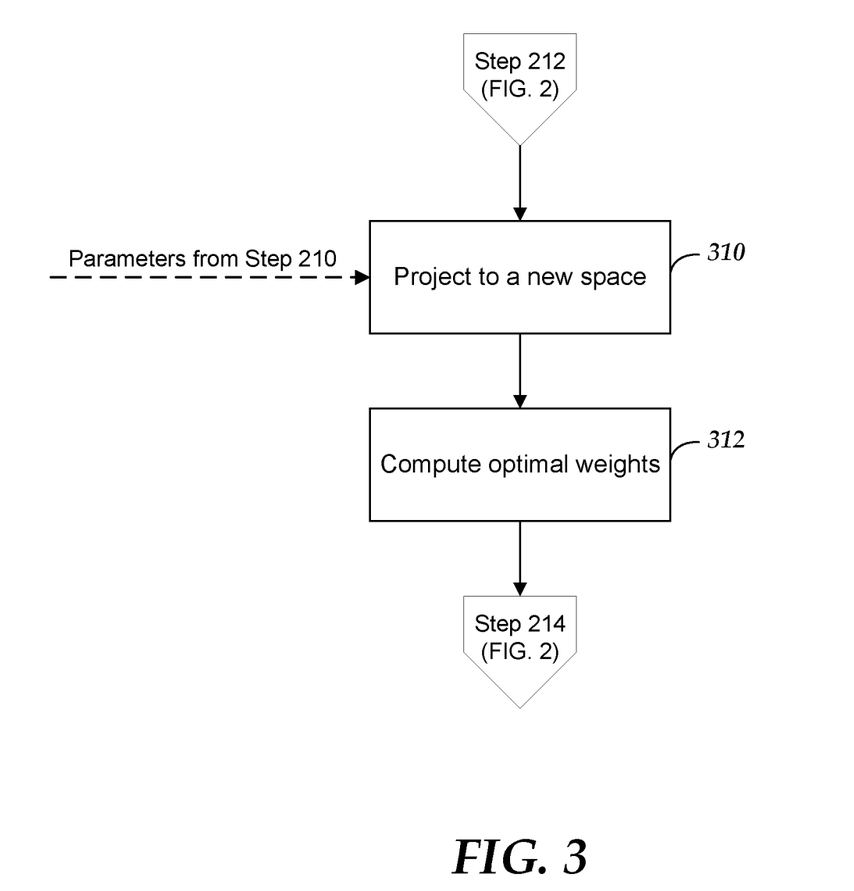
FIG. 3 is a flow diagram that illustrates one embodiment of the processing performed to develop a predictive model that predicts concentrations of COPCs.

Additional detail concerning one embodiment of step 212, which uses partial least squares regression, is provided with reference to FIG. 3.

Collectively, steps 202-212 may be referred to as a calibration process, or sub-method, in which the predictive model is calibrated against laboratory measured results, where the model is based on actual sensor data.

At step 214 the predictive model constructed at step 212 is tested or validated during the course of a validation time period or several validation time periods. Generally, the model is rerun for a COPC to be monitored with an optimized set of determined parameters. Model results generated using new multi-parameter sensor data 218 over a validation time period or periods are compared to new analytic samples 216 from a laboratory. This testing or validation may be referred to as a blind validation as the predictive model is tested against new sensor data and water samples to determine if the model accurately predicts the COPC concentration over the validation time period or periods, as measured by analytic samples 216. Additionally, step-wise cross-validation may be used, where multiple model runs are conducted with randomly selected laboratory-based data with which to calibrate and validate the model. Comparisons between modeled particulate COPCs and modeled unfiltered minus modeled filtered (dissolved) COPCs may provide further validation of component optimization results.

At step 220 a determination is made as to whether the model sufficiently predicts physically-based data. This step compares time series results, generated from the model created in step 212, which predicts concentrations of COPC over the course of a validation time interval, with analytic samples 216. Sufficient prediction may be defined and quantified by comparing modeled versus measured accuracy, error, bias, and spread against analytic field duplicate accuracy, error, bias, and spread. If the results are adequate, e.g., model error is less than a threshold value, e.g. 10% of field duplicate error, then the predictive model is complete. In this case, the model can be applied to incoming sensor data indefinitely to predict concentrations of COPCs.

A critical part of this step is to ensure that the model generates time series predictions or estimates of COPC concentrations that are physically and biogeochemically-based and not only statistically based. Thus, model-generated time series data that is physically impossible or highly unlikely will be identified and result in failing the tests at step 220 and hence repeating steps 212, 214 and 220. Examples of unlikely results that are identified in this step are listed below in Table 1.

TABLE 1

Tests for Physical-based Data

Negative COPC concentrations.
Dissolved or particulate concentrations that are higher than total (unfiltered) concentrations.
A concentration that during a tidal phase jumps up and down with high variance.
A concentration that grossly increases during a physically quiescent period (e.g., consistently low flow rate).

If the results are not adequate then the method flows to step 222 where a different set of parameters, new number of components, or both modifications are selected. After selecting a new set of parameters and/or components, processing returns to step 212. Updates to the model inputs (parameters and components) may be completed in a step-wise fashion, similar to the component selection processed as outlined in step 212.

FIG. 3 is a flow diagram that illustrates one embodiment of the processing performed to develop a predictive model that predicts concentrations of COPCs, i.e. step 212 of FIG. 2. The steps in FIG. 3 generally assume the use of a multi-parameter statistical model such as partial least squares regression (PLS regression) that combines multiple linear regression and principal component analysis (PCA), where multiple linear regression finds a combination of predictors that best fit a response and PCA finds combinations of predictors with large variance. Techniques other than regression, such as machine learning techniques and specifically Random Forests or neural networks, may also be used.

At step 310 the method accesses the set of parameters determined in either step 210 or step 222 of method 200 that describe the primary variance of a particular COPC concentration in a water column being evaluated. At this step PLS regression projects these parameters into a new mathematical space using a mathematical transformation. In the new mathematical space dimensions are based on components, which are combinations of variables that are linearly related to the measured chemical concentrations, as characterized by the analysis dataset generated in step 204.

This step is not required if the statistical model being used, e.g. multiple linear regression, that can directly correlate multiple variables with laboratory data.

At step 312 the correlation between predictions and observations are optimized to compute optimal weights for each of the set of input variables. These are applied to multi-parameter sensor time series data 208 to increase the temporal resolution of chemical concentrations. When statistical models other than PLS regression, or machine learning, are used then rather than scalar weights, the result of this step may be loadings, or factors.

The above specification, examples, and data provide a complete description of the manufacture and use of the composition of the invention. Since many embodiments of the invention can be made without departing from the spirit and scope of the invention, the invention resides in the claims hereinafter appended.

What is claimed is:

1. A computer-implemented method for monitoring natural waters, comprising:
   receiving analytic data from a laboratory, which measures a concentration of a chemical of potential concern (COPC) over a designated period of time based on samples from a water column collected at a specific location, wherein the chemical of potential concern is a hydrophobic chemical;
   receiving a time series of sensor data from each of a plurality of sensors, over the designated period of time, wherein each sensor measures a different characteristic of the water column, and wherein each sensor is submerged in the water column at the specific location, and wherein none of the sensors measure the concentration of the COPC;
   determining parameters, based on the sensor data and the analytic data, that describe a primary variance of the (COPC);
   developing a model, based on the determined parameters, that predicts a concentration of the COPC over the designated period of time;
   receiving a time series of sensor data from the plurality of sensors, the time series of sensor data corresponding to a validation time period;
   receiving analytic data that measures the concentration of the (COPC) at the specific location over the validation time period;
   running the model using the time series of sensor data corresponding to the validation time period, to predict concentrations of the COPC at the specific location over the validation time period; and
   determining whether the predicted concentrations are within a threshold value when compared to the received analytic data that measure concentrations over the validation time period.

2. The computer-implemented method of claim 1 wherein the plurality of sensors comprise at least one sensor selected from the group consisting of an absorption-attenuation meter, a conductivity-temperature-depth sensor, a fluorometer, a backscatter sensor, a turbidity sensor, a spectrometer, a spectrophotometer, a current meter, and a nutrient sensor.

3. The computer-implemented method of claim 1 wherein the chemical of potential concern is selected from the group comprising mercury (Hg), methyl mercury (MeHg), and polychlorinated biphenyls (PCBs).

4. The computer-implemented method of claim 1 wherein the model that predicts the concentration of the chemical of potential concern in the water column is a multi-parameter statistical regression model.

5. The computer-implemented method of claim 1 wherein the model that predicts the concentration of the chemical of potential concern is a partial least squares regression.

6. The computer-implemented method of claim 1 wherein determining parameters that describe the primary variance comprises selecting a subset of parameters in order to minimize errors and avoid over-constraining the model.

7. The computer-implemented method of claim 1 further comprising:
   testing whether the predicted concentrations correspond to physically-based data, and wherein a test for physically-based data includes at least one member from the group consisting of testing for a negative concentration of the chemical of potential concern, testing if a dissolved or particulate concentration is higher than a total unfiltered concentration, testing if a concentration during a tidal phase jumps up and down with high variance, and testing if a concentration grossly increases during a physically quiescent period.

8. The computer-implemented method of claim 1 further comprising:
   responsive to a determination that the predicted concentrations exceed a threshold value:
      determining new parameters that describe the primary variance;
      developing a revised model to predict concentrations of the COPC; and
      testing the model for an additional validation time period.

9. A system for monitoring and characterizing natural waters, comprising:
   a device for characterizing natural waters, comprising:
      a waterproof housing;
      a processor enclosed by the waterproof housing; and
      a plurality of sensors, enclosed by the waterproof housing, wherein each sensor provides a time series of sensor data over a designated period of time, wherein each sensor measures a different characteristic of a water column, and wherein each sensor is submerged in the water column at a specific location;
   a processing device for predicting concentrations of a chemical of potential concern, comprising:
      a data storage for (1) storing the time series of sensor data received from each of the plurality of sensors, and (2) storing analytic data from a laboratory that measures a concentration of a chemical of potential concern (COPC) over the designated period of time based on samples from the water column collected at the specific location, wherein the (COPC) is a hydrophobic chemical and wherein none of the sensors in the plurality of sensors measures the concentration of the COPC;
      a processor
      a nontransitory memory, in communication with the processor, for storing instructions, which when executed by the processor, cause the device:
         to determine parameters, based on the sensor data and the analytic data, that describe a primary variance of the (COPC);
         to develop a model, based on the determined parameters, that predicts the concentration of the COPC over the designated period of time;
         to receive a time series of sensor data from the plurality of sensors, the time series of sensor data corresponding to a validation time period;
         to receive analytic data that measures the concentration of the COPC at the specific location over the validation time period;
         to run the model using the time series of sensor data corresponding to the validation time period, to predict concentrations of the COPC at the specific location over the validation time period; and to determine whether the predicted concentrations are within a threshold value when compared to the received analytic data that measure concentrations over the validation time period.

10. The system of claim 9 wherein the plurality of sensors comprise at least one sensor selected from the group consisting of an absorption-attenuation meter, a conductivity-temperature-depth sensor, a fluorometer, a backscatter sensor, a turbidity sensor, a spectrometer, a spectrophotometer, a current meter, and a nutrient sensor.

11. The system of claim 9 wherein the chemical of potential concern is selected from the group comprising mercury (Hg), methyl mercury (MeHg), and polychlorinated biphenyls (PCBs).

12. The system of claim 9 wherein the model that predicts the concentration the chemical of potential concern in the water column is a multi-parameter statistical regression model.

13. The system of claim 9 wherein the model that predicts the concentration of the chemical of potential concern is a partial least squares regression.

14. The system of claim 9 wherein determining parameters that describe the primary variance comprises selecting a subset of parameters in order to minimize errors and avoid over-constraining the model.

15. The system of claim 9 wherein the instructions, when executed by the processor, further cause the device:

to test whether the predicted concentrations correspond to physically-based data, and wherein a test for physically-based data includes at least one member from the group consisting of testing for a negative concentration of the chemical of potential concern, testing if a dissolved or particulate concentration is higher than a total unfiltered concentrations, testing if a concentration during a tidal phase jumps up and down with high variance, and testing if a concentration grossly increases during a physically quiescent period.

16. The system of claim 9 wherein the instructions, when executed by the processor, further cause the device, responsive to a determination that the predicted concentrations exceed a threshold value:

to determine new parameters that describe the primary variance;

to develop a revised model to predict concentrations of the COPC; and to test the model for an additional validation time period.

* * * * *